US00PP17661P2

(12) United States Plant Patent
Trees

(10) Patent No.: US PP17,661 P2
(45) Date of Patent: Apr. 24, 2007

(54) ***LANTANA* PLANT NAMED 'BALUCWITE'**

(50) Latin Name: *Lantana camara*
Varietal Denomination: Balucwite

(75) Inventor: Scott C. Trees, Shell Beach, CA (US)

(73) Assignee: Ball Horticultural Company, West Chicago, IL (US)

( * ) Notice: Subject to any disclaimer, the term of this patent is extended or adjusted under 35 U.S.C. 154(b) by 9 days.

(21) Appl. No.: 11/282,550

(22) Filed: Nov. 18, 2005

(51) Int. Cl.
*A01H 5/00* (2006.01)

(52) U.S. Cl. ..... Plt./227

(58) Field of Classification Search ..... Plt./227
See application file for complete search history.

(56) References Cited

PUBLICATIONS

European Plant Breeders' Rights application No. 2005/2338 filed Nov. 16, 2005.

*Primary Examiner*—Kent Bell
(74) *Attorney, Agent, or Firm*—Audrey Charles

(57) ABSTRACT

A new and distinct cultivar of *Lantana* plant named 'Balucwite' characterized by its white-colored flowers having a yellow center, dark green-colored foliage, and very compact, upright and mounded growth habit.

1 Drawing Sheet

Latin name of genus and species of plant claimed: *Lantana camara.*
Variety denomination: 'Balucwite'.

BACKGROUND OF THE INVENTION

The present invention relates to a new and distinct cultivar of *Lantana* plant botanically known as *Lantana camara* and hereinafter referred to by the cultivar name 'Balucwite'.

The new cultivar originated in a controlled breeding program in Arroyo Grande, Calif. during May 2002. The objective of the breeding program was the development of *Lantana* cultivars with continuous flowering, dark green-colored foliage, and a well-branched, compact growth habit.

The female (seed) parent of the new cultivar was the *Lantana camara* cultivar Dwarf Pink, not patented, characterized by its pink lavender-bicolored flowers, dark green-colored foliage, and compact mounded growth habit. The male (pollen) parent of the new cultivar was the proprietary *Lantana camara* breeding selection designated BFP-303, not patented, characterized by its golden yellow-colored flowers, dark green-colored foliage, and compact mounded growth habit. The new *Calibrachoa* was discovered and selected by the inventor as a single flowering plant within the progeny of the above stated cross-pollination during November 2002 in a controlled environment at Arroyo Grande, Calif.

Asexual reproduction of the new cultivar by terminal stem cuttings since November 2002 at Arroyo Grande, Calif. and West Chicago, Ill. has demonstrated that the new cultivar reproduces true to type with all characteristics, as herein described, firmly fixed and retained through successive generations of such asexual propagation.

SUMMARY OF THE INVENTION

The following characteristics of the new cultivar have been repeatedly observed and can be used to distinguish 'Balucwite' as a new and distinct cultivar of *Lantana* plant:

1. White-colored flowers having a yellow center;
2. Dark green-colored foliage; and
3. Very compact, upright and mounded growth habit.

Plants of the new cultivar differ from plants of the female parent primarily in flower color and growth habit and from plants of the male parent primarily in flower color and growth habit.

Of the many commercially available *Lantana* cultivars known to the inventor, the most similar in comparison to the new cultivar is 'Balucwhit', U.S. Plant Pat. No. 16,523, However, in side by side comparisons, plants of the new cultivar differ from plants of 'Balucwhit' in the following characteristics:

1. Plants of the new cultivar are more compact than plants of 'Balucwhit'; and
2. Plants of the new cultivar have fewer inflorescences per plant than plants of 'Balucwhit'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balucwite'. The plants were grown in 10 cm pots for 9 weeks in a greenhouse at West Chicago, Ill.

DETAILED BOTANICAL DESCRIPTION

Figure 1:
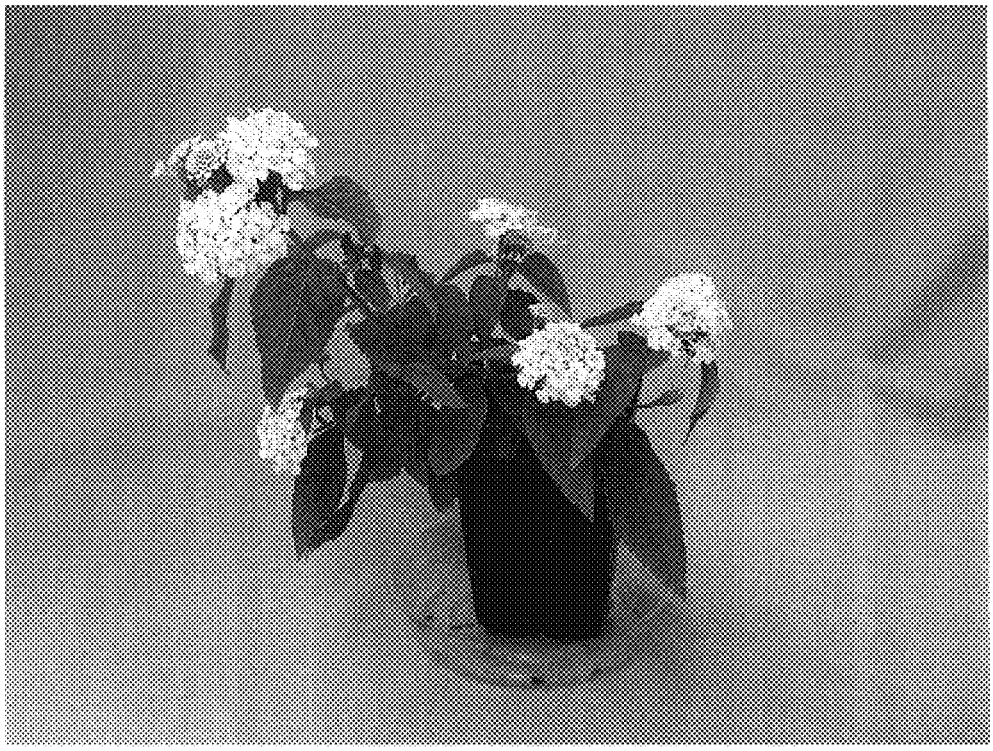
FIG. 1 illustrates a side view of the overall growth and flowering habit of 'Balucwite'.
Figure 2:
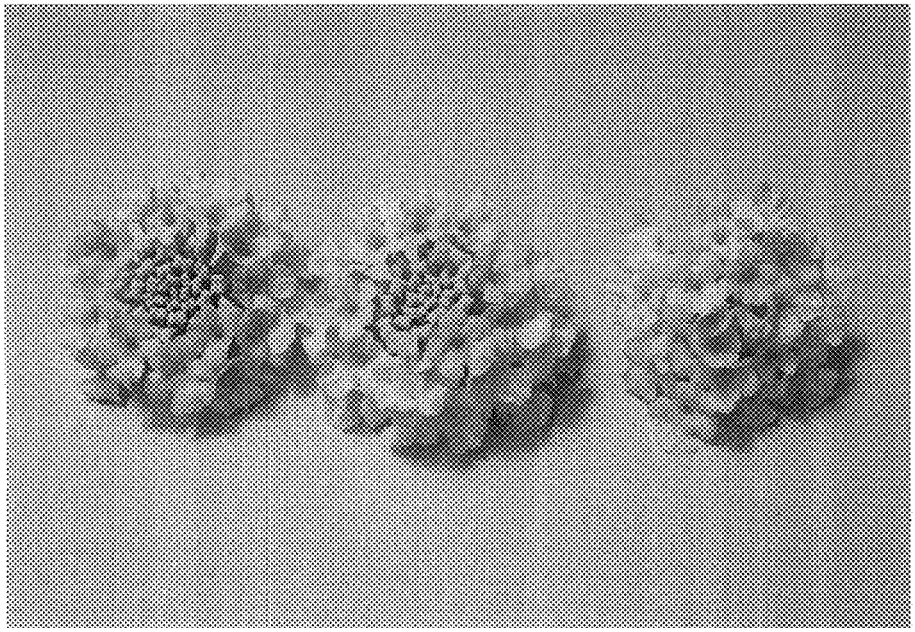
FIG. 2 illustrates a close-up view of a series of individual inflorescences of 'Balucwite' with the first open on the left to fully open on the right.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on May 20, 2005 between 3:00 p.m. and 4:00 p.m. under natural light conditions, in West Chicago, Ill.

The following descriptions and measurements describe plants produced from cuttings from stock plants and grown in a double polycarbonate-covered greenhouse under conditions comparable to those used in commercial practice. The plants were grown at West Chicago, Ill. in 10 cm pots for 9 weeks utilizing a soilless growth medium. Greenhouse temperatures were maintained at approximately 75° F. to 85° F. (24° C. to 29° C.) during the day and approximately 62° F. to 68° F. (17° C. to 20° C.) during the night. Greenhouse light levels of 4,000 to 10,000 footcandles were maintained during the day.

Botanical classification: *Lantana camara* cultivar Balucwite.

Parentage:

*Female parent.*—*Lantana camara* cultivar, Dwarf Pink, not patented.

*Male parent.*—Proprietary *Lantana camara* breeding selection designated BFP-303, not patented.

Propagation:

*Type cutting.*—Terminal stem.

*Time to initiate roots.*—Approximately 7 to 11 days.

*Time to produce a rooted cutting.*—Approximately 4 weeks.

*Root description.*—Fine, fibrous.

*Rooting habit.*—Freely branching.

Plant description:

*Crop time.*—Approximately 6 to 7 weeks from a rooted cutting.

*Growth habit and general appearance.*—Very compact, upright and mounded.

*Size.*—Height from soil level to top of plant plane: Approximately 17.4 cm. Width: Approximately 22.0 cm.

*Branching habit.*—Well-branched. Approximately 2 main branches per plant, forming lateral branches at every node. Pinching enhances basal branching.

*Branch.*—Strength: Strong, becomes woody with age. Shape: Square in cross section. Length: Approximately 17.5 cm. Diameter: Approximately 3.7 mm. Texture: Hispid. Color: 144A. Internode length at center of branch: Approximately 3.0 cm.

*Foliage.*—Number of leaves per main branch: Approximately 13. Fragrance: Strong, spicy. Form: Simple. Arrangement: Opposite. Aspect: At obtuse angle to stem. Shape: Ovate. Margin: Dentate. Apex: Acute. Base: Obtuse. Venation pattern: Pinnate. Length of mature leaf: Approximately 7.3 cm. Width of mature leaf: Approximately 3.5 mm. Texture of upper and lower surfaces: Hispid with scabrous pubescence. Color of upper surface of mature foliage: Darker than 147A with venation of 145B. Color of lower surface of mature foliage: Darker than 147B with venation of 145B. Petiole length: Approximately 1.1 cm. Petiole diameter: Approximately 1.8 mm. Petiole texture: Scabrous. Petiole color: 143B.

Flowering description:

*Flowering habit.*—'Balucwite' is freely flowering under outdoor growing conditions with substantially continuous blooming from spring through autumn and year round in greenhouse environment.

*Time to first flower.*—Approximately 10.5 weeks after sticking of unrooted cutting.

*Lastingness of individual floret.*—Approximately 3 to 5 days from full maturity.

Inflorescence description:

*Appearance.*—Type: Corymb. Aspect: Facing upward or outward. Height: 1.8 cm. Width: 3.8 cm.

*Quantity per plant.*—Approximately 4 fully open at nine weeks.

*Quantity flowers per corymb at any one time.*—Approximately 16.

*Fragrance.*—Strong, spicy.

*Peduncle.*—Strength: Strong. Shape: Square in cross section. Aspect: Acute angle to stem. Length: Approximately 3.4 cm. Diameter: Approximately 1.2 mm. Texture: Scabrous. Color: 144A.

Flower description:

*Bud rate of opening.*—Generally takes 1 to 2 days for bud to progress from first color to fully open floret. Buds open in progression from the margin to the center of the inflorescence.

*Bud just before opening.*—Shape: Rectangular. Length: Approximately 2.8 mm. Width: Approximately 3.1 mm. Color: Between 8C and 8D.

*Flower.*—Type: Salverform, self-cleaning. Aspect: Facing upward or outward. Length: Approximately 1.1 cm. Diameter: Approximately 1.0 cm.

*Petals.*—Quantity: Five non-imbricate, non-symmetrical petals with one upper petal, two lateral petals and two lower petals. Petals are fused at base forming a corolla tube. Shape: Obovate. Aspect: Slightly cupped. Appearance: Dull, velvety. Apex: Obtuse. Margin: Entire. Texture of upper and lower surfaces: Glabrous. Length of upper petal from throat: Approximately 5.3 mm. Width of upper petal: Approximately 6.5 mm. Length of lateral petal from throat: Approximately 4.5 mm. Width of lateral petal: Approximately 3.9 mm. Length of lower petal from throat: Approximately 4.5 mm. Width of lower petal: Approximately 3.2 mm. Color of upper surface when first open: Lighter than 155B at margin and closest to 14A around tube opening. Color of lower surface when first open: Lighter than 155B. Color of upper surface when fully open: Lighter than 155B at margin and 5A around tube opening. Color of lower surface when fully open: Lighter than 155B.

*Corolla tube.*—Length: Approximately 1.3 cm. Diameter at tube opening: Approximately 1.4 mm. Diameter at base: Approximately 1.0 mm. Texture of inner and outer surfaces: Glabrous at proximal end gradually becoming dense at distal end. Color of inner surface when first open: Closest to 9A. Color of inner surface when fully open: Lighter than 155D. Color of outer surface when first open: 11C. Color of outer surface when fully open: Lighter than 155D.

*Calyx.*—Shape: Tubular. Height: Approximately 2.3 mm. Diameter at tip: Approximately 1.3 mm. Diameter at base: Approximately 1.0 mm.

*Sepals.*—Quantity per flower: 5, fused at the base. Shape: Linear. Apex: Acute. Length: Approximately 2.3 mm. Width: Approximately 0.8 mm. Texture of inner surface: Densely pubescent. Texture of outer surface: Densely pubescent. Color of inner and outer surfaces: 145C.

*Bracts.*—Quantity: One per flower. Shape: Lanceolate. Length: Approximately 5.0 mm. Width: Approximately 1.0 mm. Texture of upper surface: Glabrous. Texture of lower surface: Densely pubescent. Color: 144A at apex, transitioning to 144C at base.

*Reproductive organs.*—Androecium: Stamen quantity: 4 fused to tube, two positioned above stigma and two even with stigma. Stamen length: Approximately 3.0 mm. Anther shape: Ovate, bilobed. Anther length: Approximately 0.8 mm. Anther color: 3A. Pollen amount: Moderate. Pollen color: 6A. Gynoecium: Pistil quantity: One per floret. Pistil length: Approximately 4.0 mm. Stigma shape: Elliptic. Stigma length: Approximately 0.4 mm. Stigma color: 145B. Style length: Approximately 2.5 mm. Style color: 155C. Ovary diameter: Approximately 1.1 mm. Ovary color: 150C.

*Fruit.*—Classification: Drupe. Shape. Spherical. Diameter: Approximately 5 mm. Texture: Glabrous. Color of immature fruit: 137B. Color of mature fruit: Greyer than 103B.

*Seed.*—Quantity: Sparse. Diameter: Approximately 4.0 mm. Color: Closest to 200C.

Disease and pest resistance: Resistance to pathogens and pests common to *Lantana* has not been observed.

What is claimed is:

1. A new and distinct cultivar of *Lantana* plant named 'Balucwite', substantially as herein shown and described.

* * * * *